United States Patent [19]

Feitelson

[11] Patent Number: 5,002,891

[45] Date of Patent: * Mar. 26, 1991

[54] **MULTIFUNCTIONAL PLASMID VECTORS FROM ACTINOMADURA AND *ESCHERICHIA COLI***

[75] Inventor: Jerald S. Feitelson, Englewood, N.J.

[73] Assignee: American Cyanamid Company, Stamford, Conn.

[*] Notice: The portion of the term of this patent subsequent to Jan. 8, 2008 has been disclaimed.

[21] Appl. No.: 69,330

[22] Filed: Jul. 2, 1987

[51] Int. Cl.$^5$ .............................................. C12N 15/03
[52] U.S. Cl. ........................... 435/252.33; 435/172.3; 435/252.3; 435/320.1; 935/29
[58] Field of Search ...................... 435/172.3, 320, 825, 435/849, 886, 252.3, 252.33, 252.35; 935/22, 23, 27, 29, 72, 73, 75

[56] References Cited

U.S. PATENT DOCUMENTS 4,195,079  3/1980  Celmer et al. ........................ 424/122
4,468,462  8/1984  Malin et al. ............................ 935/29

OTHER PUBLICATIONS

Katz et al., *J. Gen. Micro.*, 129:2703–2714, (1983).

*Primary Examiner*—Jacqueline Stone
*Assistant Examiner*—Marian C. Knode

[57] ABSTRACT

The present invention discloses multifunctional recombinant DNA plasmid cloning vectors able to replicate and express dominant drug resistance markers in *Escherichia coli*, Streptomyces, and Actinomadura.

10 Claims, 3 Drawing Sheets

MULTIFUNCTIONAL PLASMID VECTORS FROM ACTINOMADURA AND *ESCHERICHIA COLI*

FIELD OF THE INVENTION

The present invention provides novel recombinant DNA cloning vectors comprising two functional origins of replication. One is derived from plasmid pAkijl and the other from plasmid pBR322. In addition, these vectors contain restriction fragments conferring resistance to antibiotics on the host bacterial cells. The invention further comprises transformants of the aforementioned vectors.

BACKGROUND OF THE INVENTION

The present invention provides novel antibiotic resistance-conferring cloning vectors for use in *Escherichia coli*, Streptomyces, and Actinomadura. In the prior art the introduction, development, and exploitation of recombinant DNA technology in the latter two classes of microorganisms has been difficult, because of the absence of selectable genetic markers on cloning vectors. This has been a particular problem in the Actinomadura especially because few if any plasmid vectors have heretofore been available. The vectors in the present invention may be obtained in *Escherichia coli*, Streptomyces, and Actinomadura and therefore, represent a significant advance in the art. In addition these vectors are functional in all of these classes.

The present vectors are experimentally convenient and useful, because of their small size, cross-genus transformability, and ability to transform and be selected from any restrictionless species of Streptomyces or Actinomadura strain that is sensitive to thiostrepton. This particular drug is an excellent selective agent due to the widespread sensitivity among the Actinomycetales, its stability upon prolonged incubation, and the simple mechanism of resistance, namely a 23S ribosomal RNA methylation conferring high-level resistance due to target site modification.

SUMMARY OF THE INVENTION

Figure 1:
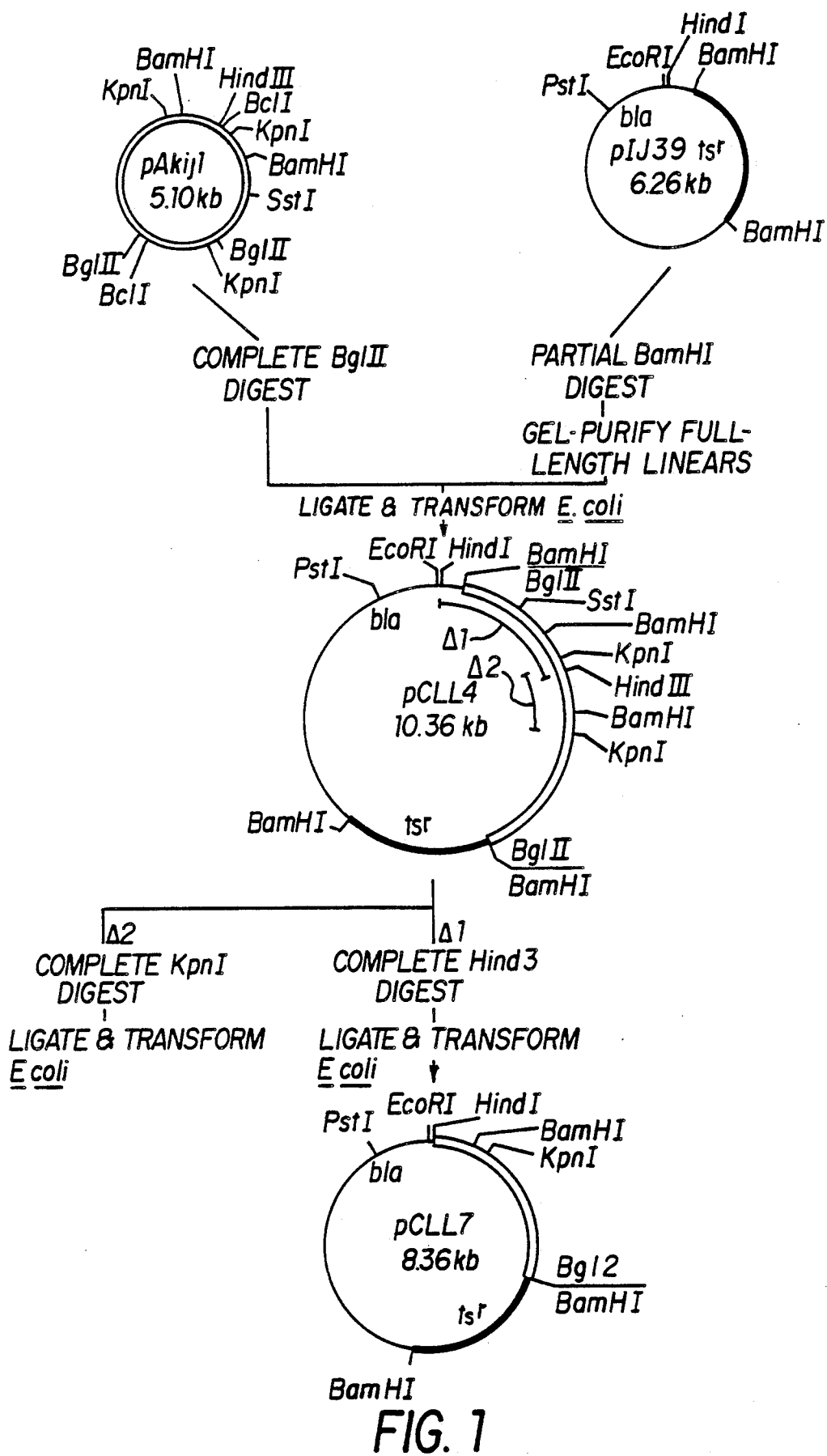
FIG. 1 is a diagram of the cloning strategy for the plasmid pCLL4 and pCLL7.
Figure 2:
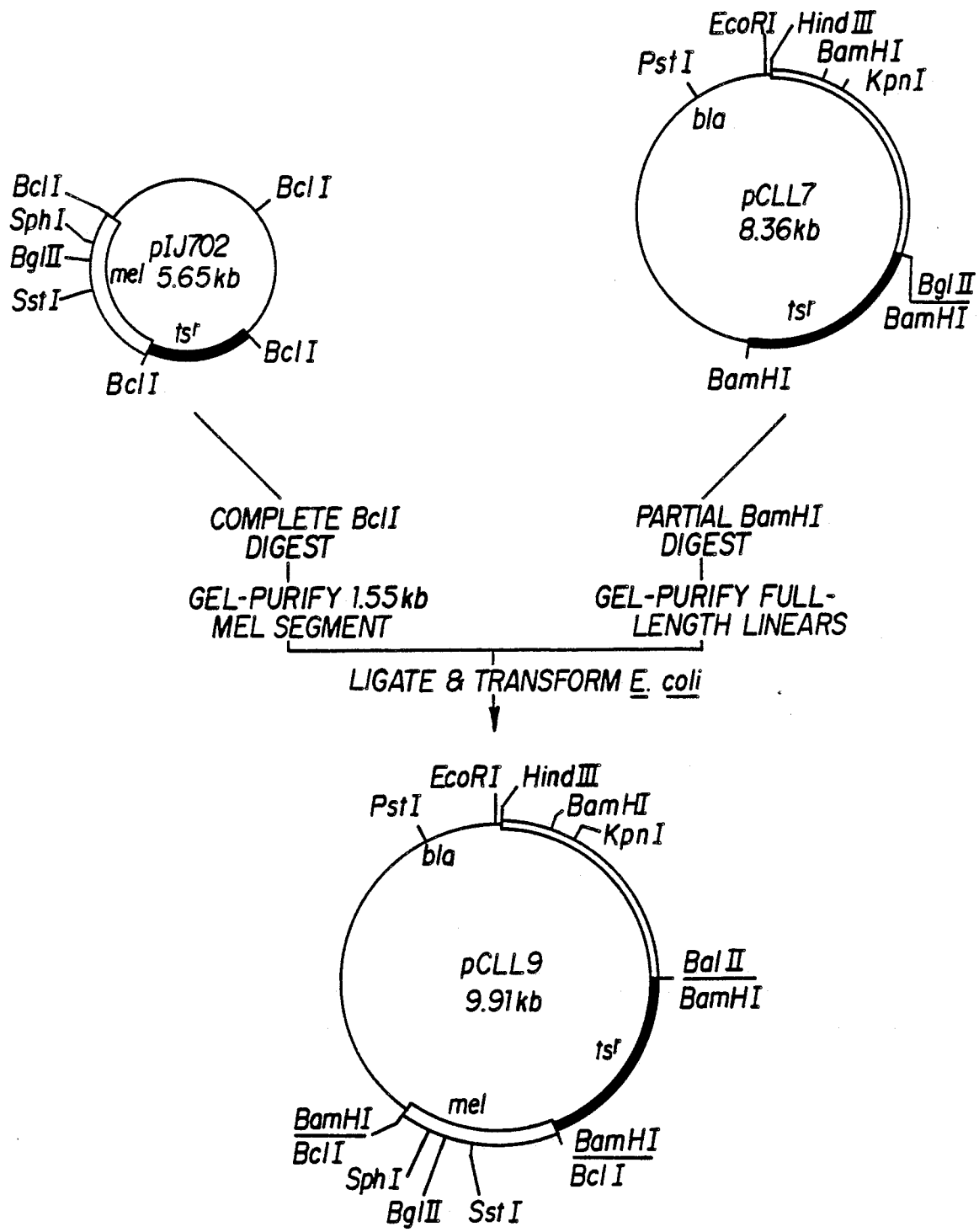
FIG. 2 is a diagram of the cloning strategy for the plasmid pCLL9.
Figure 3:
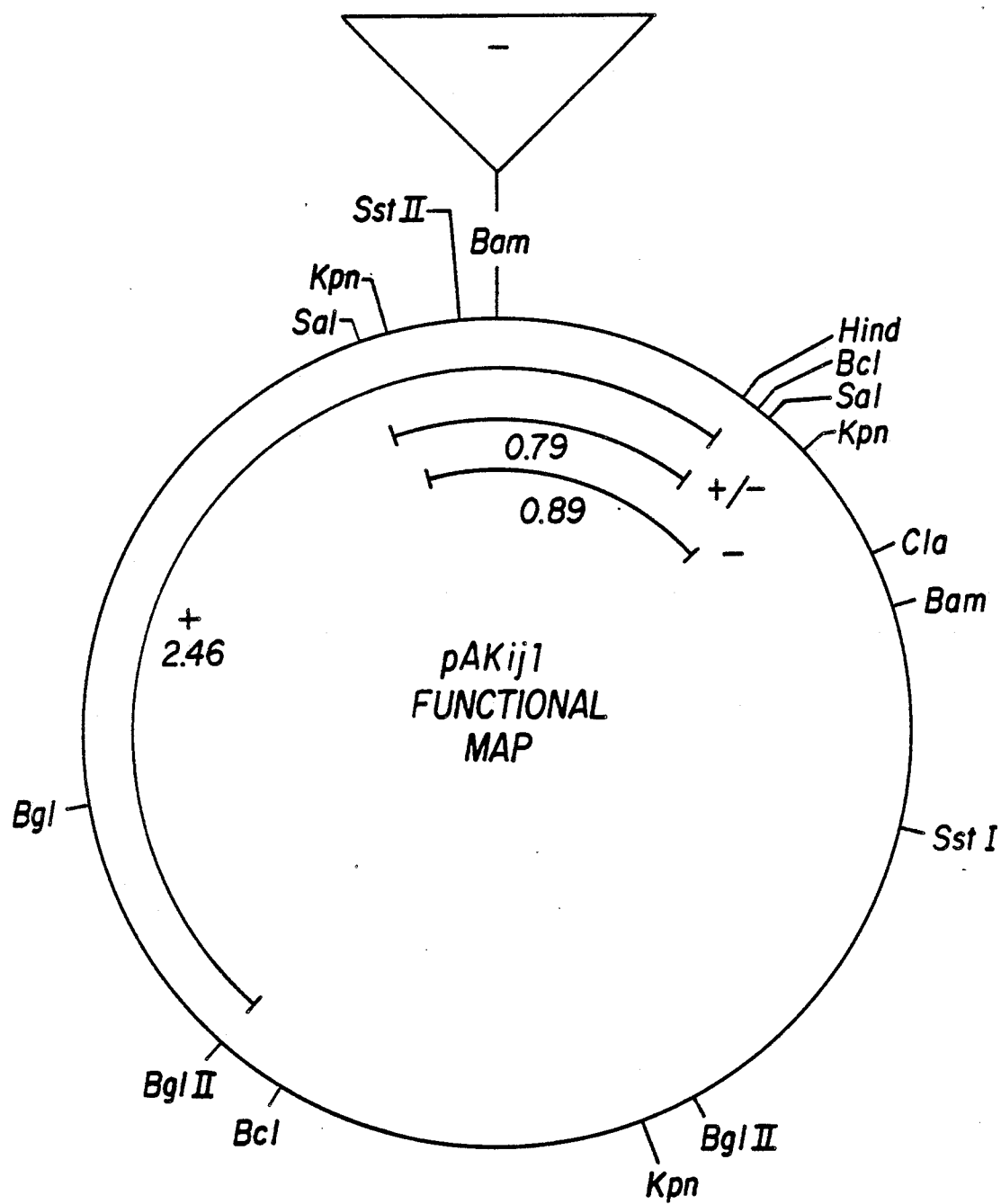
FIG. 3 is a functional map of the plasmid pAkijl.

A diagram of the cloning strategy and the resulting recombinant plasmids described in this invention is shown in FIGS. 1 and 2. A 4.10 kb portion of plasmid pAkijl, isolated from *Actinomadura kijaniata* ATCC 31588, as disclosed in copending application Ser. No. 07/069,427, was ligated to pIJ39, a previously-existing recombinant between pBR322 (Bolivar, et al. (1977) Gene 2:95) and a 1.9 kb BamHI segment encoding the thiostrepton resistance gene (Thompsone., et al. (1982) Gene 20:51). The resulting plasmid, pCLL4, was capable of replication in *Escherichia coli* and expression of resistence to ampicillin, and of replication in *Streptomyces lividans* and expression of resistance to thiostrepton. Thus, a bifunctional plasmid vector was constructed between these two widely divergent genera. These results also showed that an origin of replication from Actinomadura can function in Streptomyces, although the reverse is not necessarily true. Subsequent in vitro modification results in the deletion of a further 2 kb segment from pCLL4 without phenotypic effect, resulting in pCLL7. Finally, the addition of a 1.55 kb segment from pIJ702 (Katz, et al. (1983) *J. Gen. Micro.* 129:2703) containing the mel gene which encodes the tyrosinase enzyme yielded the 9.91 kb plasmid, pCLL9.

For convenience and illustrative purposes, the thiostrepton resistance-conferring 1.9 kb BamHI fragment from pIJ39 is ligated, along with pBR322, to the 4.10 kb BglII fragment containing the pAkijl origin of replication. Recombinant plasmids of two orientations at two different fusion sites can result from these constructions. Various plasmid pAkijl restriction fragments can be used for ligation of the antibiotic resistance-conferring DNA segments provided that the origin of replication or integration contained in the 4.10 kb BglII restriction fragment is present. Such plasmid pAkiji restriction fragments include, but are not limited to, the 2.65 kb BclI, 2.46 kb HindIII-BglII (as in pCLL7), 0.89 kb KpnI and 2.97 kb BamHI-BglII fragments. In addition, a particular antibiotic resistance-conferring DNA segment is not limited to a single position, but can be ligated or inserted into varying sites of plasmid pAkijl or deletion derivatives provided that the origin of replication or other critical plasmid controlled physiological functions are not destroyed. Those skilled in the art can easily determine which sites are suitable for the ligation or insertion of particular DNA segments.

Although the 1.90 kb BamHI thiostrepon resistance-conferring DNA segment from pIJ39 is used as an example, those skilled in the art can construct and use other segments, individually or in combination to confer antibiotic resistance to recombinant vectors based on Actinomadura plasmid origins of replication. For example, the 1.05 kb BclI subfragment of the 1.90 kb BamHI thiostrepton resistanceconferring restriction fragment could be used in other constructions. Still other DNA segments conferring resistance to other antibiotics such as, for example, viomycin, erythromycin, neomycin, hygromycin, ribostamycin, novobiocin, destomycin, racemomycin, tylosin, chloramphenicol, and the like can also be constructed and used by those skilled in the art. In addition, functional derivatives of these or any of the other antibiotic resistance-conferring DNA segments herein described can be constructed by adding, deleting, or changing certain nucleotides in accordance with the genetic code. Those skilled in the art will understand that ligation of these derivatives, or any other antibiotic resistance-conferring DNA segment, to plasmid pAkijl origin of replication-containing fragment in vectors are also within the scope of the present invention.

Modifications of pAkijl-based vectors can be made to facilitate their use in ligations. For example, synthetic molecular linkers can be provided to alter cloning sites, or site-specific mutagenesis can be used to specifically alter the nucleotide sequences of the origin of replication or other regions of the plasmid as desired. Those skilled in the art understand nucleotide chemistry and the genetic code and thus which nucleotides are interchangeable and which DNA modifications are desirable for a specific purpose.

The multifunctional nature of the constructions described herein are particularly advantageous because yield and plasmid manipulation can be done faster and more conveniently in *Escherichia coli* than in Streptomyces or Actinomadura. In addition, genetic manipulations such as gene fusions or transposon mutagenesis are simply accomplished in *Escherichia coli* by standard techniques, whereupon functional analysis can subsequently be done by transformation into Streptomyces or Actinomadura.

The recombinant DNA cloning vectors of the present invention are not limited to use in a single species or strain of the Actinomycetales such as the Streptomyces or Actinomadura. The vectors are broadly applicable and can be introduced by transformation into host cells of many Streptomyces or Actinomadura taxa, particulary restrictionless strains of economically important taxa that produce antibiotics such as polyether, aminoglycoside, macrolide, beta-lactam, and glycopeptide antibiotics. Such restrictionless strains are readily selected and isolated from Actinomycetes by conventional phage-based procedures (e.g., Lomovskaya et al., *Microbiol. Rev.* 44:206), or by mutagenesis followed by transformation with a normally restricted plasmid carrying a dominant selectable marker (Matsushima, et al. (1987) *Mol. Gen. Genet.* 206:393). Host cells or restrictionless strains lack endogenous restriction enzymes and therefore can be transformed with a greatly enhanced frequency. For purposes of the present invention, host cells containing restriction enzymes that do not cut any of the restriction sites of the present vectors are also considered restrictionless.

Because the origin of replication isolated from plasmid pAkijl of *Actinomadura kijaniata* is capable of directing the replication of plasmids in Streptomyces and Actinomadura, it is also useful and may be transformed into cells of restrictionless strains of other taxa, such as Bacillus, Staphylococcus, and other Actinomycetes, including Streptosporangium, Actinoplanes, Nocardia and Micromonospora. The origin of replication derived from pBR322 is capable of replication in *Escherichia coli*, as well as a variety of other gram-negative species. Thus, the vectors of the present invention have wide applicability and can be used as cloning vectors into host cells of a very large variety of microorganisms.

While all the embodiments of the present invention are useful, some of the present recombinant DNA cloning vectors and transformants are preferred. Accordingly, preferred vectors are plasmids pCLL4, pCLL7, and pCLL9, and preferred transformants are *Escherichia coli* ATCC 67,447 (pCLL4); *Escherichia coli* ATCC 67,448 (pCLL7) and *Escherichia coli* ATCC 67,449 (pCLL9).

The recombinant DNA cloning vectors and transformants of the present invention have broad utility and are novel particularly for filling the need for suitable cloning vectors for use in the Actinomadura, a little studied but economically important genus among the Actinomycetes. The ability of the present vectors to confer antibiotic resistance, particularly to thiostrepton, to strains that are normally killed by the agent provides a very powerful method for selecting rare transformants. Most importantly, foreign DNA cloned into the present vectors and propagated in high yield in *Escherichia coli* can then subsequently be introduced into appropriate Actinomycetes or other strains by standard techniques and transformants isolated by the appropriate antibiotic selection.

In addition to the ability to select for antibiotic resistance in Actinomycetes allowing for the efficient isolation of extremely rare cells containing the particular non-selectable DNA of interest, the markers also insure that the cloned DNA segments are stably maintained in host cells during prolonged fermentation. Those cells which lose the recombinant plasmid cannot grow under continued antibiotic (e.g. thiostrepton) selection, and are rapidly lost from the culture. The covalently linked DNA will enjoy the opposite fate of stable maintenance if the vector resides in a host which is exposed to levels of antibiotic which are normally toxic to non-transformed or cured cells. Thus, the vectors of the present invention can stabilize and maintain any DNA sequence of interest.

Several convenient cloning sites are available in non-essential regions of the vectors, perhaps most usefully at the BglII site in pCLL9. In shotgun cloning experiments to isolate new genes, or subcloning experiments to characterize existing genes, pCLL9 can be cleaved at its unique BglII site, and donor DNA cleaved with any member of a set of restriction enzymes - BamHI, BclI, BglII, MboI, Sau3A, or XhoII - which all generate 5'-GATC cohesive tails ('sticky ends') which can join with each other and so render the ends of the vector molecule unable to ligate with each other to reconstitute the vector. The vector can be treated with calf intestine alkaline phosphatase to remove 5'-phosphate groups. Any surviving intact vector molecules will transform the appropriate host cell with a Mel$^{30}$ phenotype, and thus black colonies can be screened out.

Other useful cloning sites include the unique SstI site in pCLL9, with properties similar to that of the BglII site in the mel gene; the PstI site in the pBR322 moiety of pCLL4, pCLL7, and pCLL9 is also available for cloning in Streptomyces and Actinomadura, but is located in the bla gene eliminating the remaining selectable marker in *Escherichia coli*.

DETAILED DESCRIPTION OF THE INVENTION

The present invention comprises recombinant DNA cloning vectors comprising:
1. two functional origins of replication, one from pBR322 and the other from pAkijl,
2. one or more DNA segments that confer resistance to at least one antibiotic when transformed into a sensitive host cell, said host cell being susceptible to transformation, cell division, and culture.
3. one or more restriction endonuclease sites located in portions of the cloning vector non-essential for replication or expression of drug resistance. These are cloning sites for the in vitro insertion of foreign DNA.

The invention further comprises transformants of the aforementioned vectors.

EXAMPLE

Construction of the pCLL4 Series

The vectors of the present invention are initially constructed by ligating the origin of replication-containing BglII restriction fragment of pAkijl (molecular size: 4.10kb) to a partially BamHI-digested preparation of pIJ39 (molecular size: 6.26 kb). The ligation mix was introduced by transformation into competent cells of *Escherichia coli* k12 W5445 (Feitelson (1985) *J. Gen. Micro.* 131:2431), and transformants selected by their resistance to ampicillin. Forty-eight ampicillin resistant clones are screened by rapid plasmid isolation techniques for plasmids larger than pIJ39. Four clones contain recombinant plasmids of the desired composition, having a molecular size of 10.36kb, the sum of the two reactant plasmids. Subsequent restriction mapping with BamHI and HindIII placed the four pCLL4 plasmids into three classes.

A clone was isolated which contains the plasmid identified as pCLL4 whose restriction map appears in FIG. 1.

Therefore, three out of the four possible sites and orientations of the ligation of pAkijl/BglII to the pIJ39-/BamHI partial digest are recovered. This plasmid is selected for further analysis and manipulation because of the convenient locations of its restriction sites, and deposited as ATCC 67,447.

To test whether the pAkijl-derived portion of pCLL4 would enable the plasmid to function in Streptomyces, DNA is introduced by transformation into protoplasts of *Streptomyces lividans*, with selection for thiostrepton resistance. Surprisingly, there is a high efficiency of transformation of *Streptomyces lividans* using *Escherichia coli*-derived pCLL4. This result proves that the origin of replication isolated from the Actinomadura plasmid, pAkijl, functions in Streptomyces, and provides an experimentally convenient method to further localize the functional origin of replication.

Construction of pCLL7

As shown in FIG. 1, there are two in vitro deletions made in pCLL4 in order to test for non-essential DNA. The first (Δ1) is a 1.99 kb HindIII deletion extending 346 base pairs into pBR322 and 1.64 kb into the pAkijl sequence. The small pBR322 deletion is not expected to result in any phenotypic effect, as the tetracycline resistance gene already is inactivated and this region is known to contain the tetracycline resistance gene promoter (Widera, et al. (1978) *Mol. Gen. Genet.* 163:301). However, removal of 40% of the pAkijl sequence could easily have eliminated the origin of replication, and thus prevented successful transformation of *Streptomyces lividans*.

*Escherichia coli* (ATCC 67,447)-purified pCLL4 is digested to completion with HindIII, and ligated at low DNA concentration to favor circularization of the 8.36 kb fragment. The mixture is introduced by transformation into competent *Escherichia coli* cells, ampicillin-resistant colonies selected, and sixteen are screened for plasmids smaller than pCLL4. Fifteen out of sixteen clones contain plasmids which have a molecular size of 8.36 kb. Digestion of one plasmid preparation with HindIII confirms the expected structure.

The resulting plasmid, pCLL7, which is shown in FIG. 1, is able to transform *Streptomyces lividans* protoplasts to thiostrepton resistance with high efficiency, and proves that the 1.64 kb deleted region from the HindIII site to the BglII site in pAkijl is not necessary for replication.

Construction of pCLL8

In a manner similar to that used to construct and test pCLL7, the second deletion (Δ2) is made in vitro to pCLL4 by complete digestion with KpnI and self circularization. This results in about a 890 bp deletion near the middle of the pAkijl sequence, and slightly overlaps with the previously described HindIII deletion in pCLL7. Again, fifteen out of sixteen ampicillin-resistant *Escherichia coli* transformants contain plasmids smaller than pCLL4, and have only one site for KpnI. The resulting plasmid, pCLL8, has the expected molecular size of 9.4 kb, but is completely unable to transform *Streptomyces lividans* protoplasts to thiostrepton resistance. This result suggests that the small KpnI deletion eliminates sequences essential to replication in Streptomyces, and narrows down the origin of replication of pAkijl to between the HindIII site and overlaps the KpnI site. This interpretation is further supported by the insertional inactivation of replication of pCLL7 in Streptomyces by cloning at the BamHI site removed in pCLL8 (see below). Thus, the origin of replication has been localized to a sequence of less than 2.46 kb (HindIII-BglII), and possibly as small as 730 bp (HindIII-KpnI).

Construction of pCLL9

A highly desirable feature of a cloning vector is the ability to easily distinguish, by a genetic test, clones carrying recombinant DNA from those which simply contain intact vector molecules. This is usually done by constructing plasmid vectors containing two drug resistance genes; cloning into one of the markers inactivates it, but selection can still be applied for the other marker. This is the principle of insertional inactivation, an example of which is found with pBR322 (Bolivar, et al., supra). Plasmid pIJ39 has a BamHI thiostrepton resistance fragment which inactivated the plasmid tetracycline resistance gene, but selection can still be exerted in *Escherichia coli* because of the intact ampicillin resistance gene (bla). In Streptomyces, a very useful gene to employ for insertional inactivation is mel, which codes for tyrosinase. Tyrosinase catalyzes the conversion of tyrosine to black melanin pigment. There are three useful cloning sites within the mel fragment: SphI, SstI, and BglII. The function of the gene is destroyed when DNA is inserted into it at any of these sites and the transformed colonies can easily be identified by their color. Transformants harboring the unaltered vector plasmid containing mel form black colonies when grown on tyrosine-containing regeneration plates because they can convert tyrosine into melanin; recombinant plasmids produce colonies of white cells.

The strategy for simultaneously deleting a BamHI site in pCLL7 and introducing the mel gene is shown in FIG. 2. There are two possible sites of insertion using partial BamHI digests of pCLL7: one at the junction of the tsr (thiostrepton resistance gene) fragment and pBR322, and the other in the pAkijl sequence previously suggested to be essential for replication in Streptomyces. Gel-purified DNA from pIJ702 (Katz, et al. supra) containing the 1.55 kb BclI fragment encoding the mel gene is ligated to partially BamHI-digested pCLL7, and introduced by transformation into a competent *Escherichia coli*. A total of 156 ampicillin-resistant *Escherichia coli* clones are screened for plasmid DNA larger than pCLL7; four have the predicted size of 9.91 kb. One clone (pCLL9) was deposited as ATCC 67,449.

Both physical (Southern Blot Hydridization Analysis) and genetic (retransformation into *Escherichia coli*) data suggest that the plasmids pCLL4 and pCLL7 at least partially integrate into the chromosome of *Streptomyces lividans*. These results suggest that the vectors will prove useful for the stable insertion of foreign genes into Streptomycetes and other Actinomycetales.

A portion of the plasmid pAverl may also be ligated to pIJ39 using the procedures set forth herein above to obtain a novel plasmid that may be used as described herein.

All of the referenced applications and publications are hereby incorporated by reference.

I claim:

1. A recombinant DNA closing vector which comprises:
   (a) a functional origin of replication from pBR322 and a functional origin of replication from pAkijl;
   (b) one or more DNA segments that confer resistance to at least one antibiotic when transformed into a sensitive host cell, said host cell being susceptible to transformation, cell division and culture; and
   (c) one or more restriction endonuclease sites in portions of the cloning vector which is non-essential for replication or expression of drug resistance.
2. The recombinant plasmid pCLL4.
3. The recombinant plasmid pCLL7.
4. The recombinant plasmid pCLL9.
5. A transformed *Escherichia coli* host cell containing the plasmid of claim 2.
6. A transformed *Escherichia coli* host cell containing the plasmid of claim 3.
7. A transformed *Escherichia coli* host cell containing the plasmid of claim 4.
8. A transformed host cell as defined in claim 5, wherein said cell is *Escherichia coli* ATCC 67447.
9. A transformed host cell as defined in claim 6, wherein said cell is *Escherichia coli* ATCC 67448.
10. A transformed host cell as defined in claim 7, wherein said cell is *Escherichia coli* ATCC 67449.

* * * * *